(12) United States Patent
Hamuro et al.

(10) Patent No.: US 10,065,019 B2
(45) Date of Patent: Sep. 4, 2018

(54) STRAIN RELIEF AND CATHETER WITH STRAIN RELIEF

(71) Applicant: Terumo Kabushiki Kaisha, Tokyo (JP)

(72) Inventors: Kota Hamuro, Shizuoka (JP); Hiroyoshi Ise, Elkton, MD (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 546 days.

(21) Appl. No.: 13/711,791

(22) Filed: Dec. 12, 2012

(65) Prior Publication Data

US 2013/0150807 A1 Jun. 13, 2013

(30) Foreign Application Priority Data

Dec. 12, 2011 (JP) ................. 2011-271580

(51) Int. Cl.
*A61M 5/00* (2006.01)
*A61M 25/00* (2006.01)
*F16L 57/00* (2006.01)
*H01R 13/58* (2006.01)

(52) U.S. Cl.
CPC ......... *A61M 25/0097* (2013.01); *F16L 57/00* (2013.01); *H01R 13/5841* (2013.01); *A61M 2025/0098* (2013.01)

(58) Field of Classification Search
CPC .............. A61M 25/0097; A61M 25/00; A61M 2025/0098; F16L 57/00; H01R 13/5741; H01R 13/5841
USPC ................. 285/114; 604/264, 525, 534, 905; 128/912; 600/127, 142
See application file for complete search history.

(56) References Cited

U.S. PATENT DOCUMENTS

| | | | |
|---|---|---|---|
| 5,076,656 A | 12/1991 | Briggs et al. | |
| 5,094,552 A * | 3/1992 | Monroe | G02B 6/3887 385/76 |
| 5,466,230 A | 11/1995 | Davila | |
| 6,068,622 A | 5/2000 | Sater et al. | |
| 6,228,073 B1 | 5/2001 | Noone et al. | |

(Continued)

FOREIGN PATENT DOCUMENTS

| | | |
|---|---|---|
| CN | 102215896 A | 10/2011 |
| JP | 4-291215 A | 10/1992 |

(Continued)

OTHER PUBLICATIONS

The extended European Search Report for the related European Application No. 12195466.3 dated Feb. 22, 2013.

(Continued)

*Primary Examiner* — Kevin C Sirmons
*Assistant Examiner* — Tiffany Legette-Thompson
(74) *Attorney, Agent, or Firm* — Kenealy Vaidya LLP

(57) ABSTRACT

Disclosed herein is a strain relief having a plurality of enclosing parts arranged in an axial direction and enclosing a longitudinal axis of the strain relief. A space portion can be formed between adjacent enclosing parts so that the strain relief is freely bendable. In the strain relief, the adjacent enclosing parts are interconnected, and one or both of opposed surfaces of the adjacent enclosing parts can be provided with a projection that projects in a direction substantially parallel with the longitudinal axis.

18 Claims, 4 Drawing Sheets

(56) References Cited

U.S. PATENT DOCUMENTS

| | | | |
|---|---|---|---|
| 6,273,404 B1 | 8/2001 | Holman et al. | |
| 6,447,462 B1* | 9/2002 | Wallace et al. | 600/561 |
| 6,503,244 B2 | 1/2003 | Hayman | |
| 2001/0049519 A1* | 12/2001 | Holman et al. | 604/534 |
| 2002/0038129 A1* | 3/2002 | Peters | A61B 17/32002 |
| | | | 606/167 |
| 2005/0060016 A1 | 3/2005 | Wu et al. | |
| 2005/0061697 A1 | 3/2005 | Moberg | |
| 2010/0069882 A1 | 3/2010 | Jennings et al. | |

FOREIGN PATENT DOCUMENTS

| | | |
|---|---|---|
| JP | 2007-521105 A | 8/2007 |
| WO | 03/026535 A2 | 4/2003 |

OTHER PUBLICATIONS

Chinese Office Action for the related Chinese Patent Application No. 201210533807.2 dated Jun. 5, 2014.
Japanese Office Action for the related Japanese Patent Application No. 2011-271580 dated Aug. 18, 2015.

\* cited by examiner

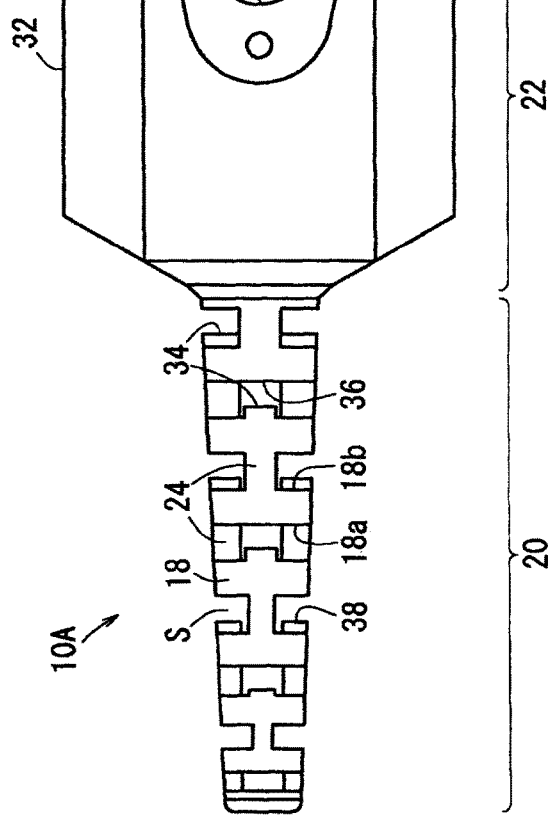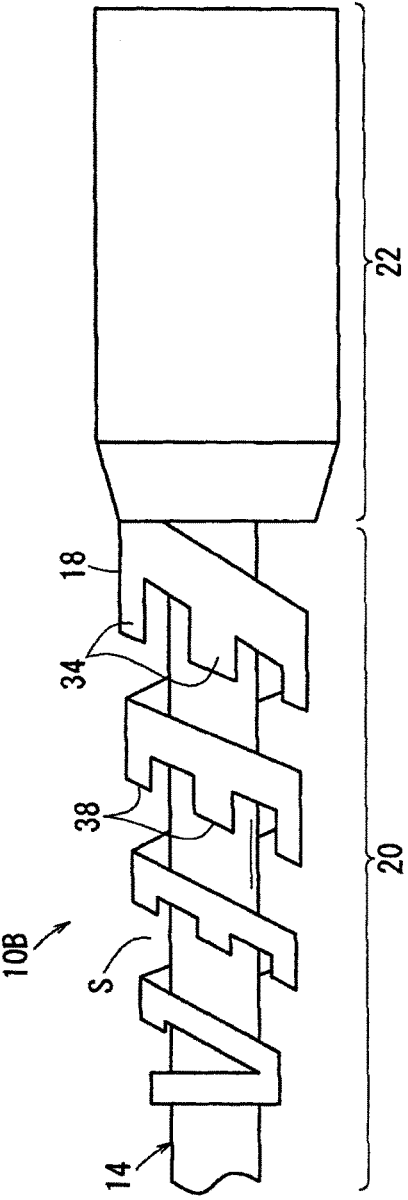
FIG. 4A
FIG. 4B

STRAIN RELIEF AND CATHETER WITH STRAIN RELIEF

This application claims the priority benefit under 35 U.S.C. § 119 of Japanese Patent Application No. 2011-271580 filed on Dec. 12, 2011, which is hereby incorporated in its entirety by reference.

BACKGROUND

The presently disclosed subject matter relates to a strain relief for reducing burden on a connection part between two members, and a catheter provided with the strain relief.

In general, a catheter for use in the medical field has a long flexible (bendable) shaft section (tubular body), and a rigid hub connected (joined) to a proximal portion of the shaft section. When used (operated), the catheter is liable to stress concentration at the connection part between the shaft section and the hub, possibly resulting in damage due to bending of the shaft section (this phenomenon is sometimes called kinking). To cope with this problem, a strain relief for enhancing the strength of the connection part between the shaft section and the hub is often provided at the connection part.

For example, U.S. Pat. No. 6,068,622 (hereinafter referred to as Patent Document 1) discloses a strain relief provided with a strain relief coil which, during use, encloses a proximal-side circumferential surface of a catheter body. The strain relief coil is a continuous coil of constant or variable pitch having coil turns that decrease in diameter from the proximal strain relief coil end to the distal strain relief coil end. The turns of the strain relief coil are preferably molded over a distal portion of exterior surface of the catheter body in the catheter hub/body junction and adhered in a spiral pattern to the exterior surface of the catheter body. In this strain relief, each turn of the coil comes closer to and further away from an adjacent turn in the coil through elastic deformation. The axial distance between coil turns (i.e., pitch) can vary along the axial length, and the strain relief as a whole is curved.

Another strain relief disclosed in U.S. Published Patent Application No. 2001/0049519 (hereinafter referred to as Patent Document 2) includes a plurality of grooves which enclose a shaft section (tube). In the strain relief disclosed in Patent Document 2, the width and spacing of the grooves may be varied to effect the flexibility of strain relief. Each groove extends through the strain relief leaving a thin portion of strain relief disposed between oppositely disposed grooves. This strain relief is more flexible at a distal end than at its proximal end. The thin portion provides a point of flexibility or transverse hinge in the strain relief. When a generally transverse bending force is applied to the strain relief, grooves on the opposite side of strain relief from the bending force will tend to close as grooves on the same side of the strain relief as the force tend to open. In short, the strain reliefs disclosed in Patent Documents 1 and 2 are so configured as to elastically support the shaft section and to disperse the load exerted on the connection part between the shaft section and the hub, thereby restraining the kinking phenomenon.

SUMMARY

When delivering a catheter to a blood vessel or the like in a living body, the catheter is moved to the target position while bending a shaft section (tubular body) of the catheter in conformity with the shape of the meandering blood vessel or the like. Therefore, the strain relief is required to bend with adequate flexibility, while suppressing (dispersing) the load exerted on the shaft section on which the strain relief is arranged.

The strain reliefs disclosed in Patent Documents 1 and 2, however, are disadvantageous in that the certain structures of the strain relief are moved closer to and away from each other comparatively easily because of the presence of spaces between the certain structures and, therefore, the strain relief as a whole may be excessively bent. Such an excessive bending of the strain relief leads to exertion of an excessive load on the connection part between the shaft section and the hub during catheter manipulation. In addition, excessive bending prevents smooth transmission of the operating forces (forces for advancement or retraction or rotation) to the shaft section.

In order to avoid the above-described excessive bending, it may be contemplated to reduce the width of the space between adjacent structures in the strain relief. This approach, however, produces another problem in that the close arrangement of the adjacent structures increases bending strength, thereby changing the flexibility of the strain relief. As a result, it becomes difficult to select the material and design the shape for the strain relief.

The presently disclosed subject matter has been made in consideration of the above-mentioned and other problems and general characteristics of the conventional art. Accordingly, an aspect of the presently disclosed subject matter includes a strain relief by which excessive bending of a connection part can be prevented and operability can be thereby enhanced. The strain relief can have a simple configuration without changing the overall flexibility. In addition, a catheter can be provided with the strain relief.

In accordance with another aspect of the presently disclosed subject matter, strain relief can include a plurality of enclosing parts arranged in an axial direction and enclosing an axis, with a space portion formed between the adjacent enclosing parts so that the strain relief is freely bendable, wherein the adjacent enclosing parts are interconnected, and one or both of opposed surfaces of the adjacent enclosing parts are provided with a projection projected in the axial direction.

According to the above-mentioned configuration, the enclosing parts have the projections projecting in the axial direction. This ensures that when the strain relief is curved, the variation amount of the space portion can be easily changed because the projection comes into contact with the enclosing part opposed thereto. In other words, the projection determines the amount of curvature of the adjacent enclosing parts, thereby regulating the degree of curvature of the strain relief while maintaining the flexibility of the strain relief. Therefore, the strain relief can prevent excessive bending of the connection part between different-hardness members (e.g., a tubular body and a hub of a catheter) while permitting the connection part to exhibit a sufficient anti-kinking property. As a result, the strain relief ensures that, for example during operation in conjunction with, for example, a catheter, operating forces can be easily transmitted to a tubular body (i.e., the catheter) and operability can thereby be enhanced.

The projection can extend or be projected at a position continuous with an outer circumferential surface of the enclosing part.

With the projection formed at a position continuous with the outer circumferential surface of the enclosing part, the projecting amount of the projection can be as small as possible, while realizing a desired degree of curvature when the strain relief is curved or is bent during use. Thus, the rigidity of the projection can be easily secured and the strain relief can be easily formed.

A plurality of the space portions can be formed in the axial direction, and the distances between end faces of each of the projections and the enclosing parts opposed to each other (in the plurality of space portions) can be substantially equal.

Where the distances between the opposed end faces of the projection and the enclosing part in the plurality of space portions are thus substantially equal, the variation amounts (the amounts of curvature of the enclosing parts) of the plurality of space portions arranged in the axial direction can be made even. Therefore, the stress exerted on the strain relief can be entirely dispersed, whereby durability of the strain relief can be enhanced.

In this case, the end faces of the projections and the end faces of the enclosing parts may be mutually formed to have a flat shape or surface.

Where the end faces of the projections and the end faces of the enclosing parts are thus mutually formed flat, the flat end faces come into contact with each other when the strain relief is curved or bent during use. As a result, the strain relief can be favorably curved, with torsion or the like restrained or limited.

The adjacent enclosing parts can be interconnected by a pair of interconnecting parts extending in the axial direction. The pairs of the interconnecting parts can be arranged alternately with the enclosing parts in the axial direction, and can be formed to gradually increase in cross-sectional area along the direction from the distal side toward the proximal side. The pairs of the interconnecting parts which are adjacent to each other with the enclosing part therebetween can deviate from each other by about 90 degrees along a circumferential direction.

When the pairs of interconnecting parts are formed as described above so as to gradually increase in cross-sectional area along the direction from the distal side toward the proximal side, the strength of the strain relief on the proximal side can be enhanced to a greater extent (as compared to the distal side). In addition, where the pairs of the interconnecting parts which are adjacent to each other with the enclosing part therebetween are deviated from each other by about 90 degrees in the circumferential direction, the tubular body can be surrounded by the interconnecting parts at angular intervals of 90 degrees. This enables the tubular body to be curved or bent during operation substantially evenly in all directions.

According to an embodiment of the presently disclosed subject matter, there is provided a catheter provided with the above-described strain relief, wherein the catheter includes a tubular body extending in the axial direction and having a hollow inside, and a hub connected to a proximal portion of the tubular body. The strain relief has enclosing parts enclosing an outer circumference of a proximal portion of the tubular body so as to dispose the tubular body at the axis, and has a proximal-side end portion of the strain relief engaged with the hub so that the distal side can be freely bent relative to the hub.

The configuration wherein the strain relief has the enclosing parts enclosing the outer circumference of the proximal portion of the tubular body of the catheter and has the proximal-side end portion thereof engaged with the hub so that the distal side can be freely bent relative to the hub, ensures that excessive bending of the connection part between the tubular body and the hub can be prevented by the projections of the enclosing parts. Consequently, operability of the catheter can be enhanced.

Further, the catheter can be configured such that the tubular body and the hub are composed as separate bodies, and that the proximal-side end portion of the strain relief includes a wing-shaped part operable to rotate the catheter, and an accommodation part in which the hub is detachably engaged and held.

With the tubular body and the hub thus composed as separate bodies, it is possible to fabricate the catheter by combining different materials. Therefore, the tubular body and the hub can be easily designed to have desired values of hardness, and the tubular body and the hub thus differing in hardness can be easily connected to each other by the strain relief. Besides, because it is not necessary to provide the hub with a wing-shaped part, the overall length of the catheter can be reduced. Consequently, in regard of the length of a shaft to be exposed from a catheter proximal end of a therapeutic device (e.g., balloon catheter) to be inserted into the catheter, a longer shaft length can be secured.

According to the presently disclosed subject matter, excessive bending of the connection part can be prevented and operability of the catheter can thereby be enhanced, with a simple configuration of the strain relief and without changing the flexibility of the strain relief.

BRIEF DESCRIPTION OF THE DRAWINGS

These and other characteristics, features, and advantages of the presently disclosed subject matter will become clear from the following description with reference to the accompanying drawings, wherein:

FIG. 4A is a lateral view showing another strain relief made in accordance with principles of the presently disclosed subject matter, and FIG. 4B is a lateral view showing yet another strain relief made in accordance with principles of the presently disclosed subject matter.

DETAILED DESCRIPTION

Now, exemplary embodiments of a strain relief and strain relief systems made in accordance with principles of the presently disclosed subject matter will be described in detail below and referring to the accompanying drawings. One exemplary embodiment relates to a catheter provided with the strain relief.

Figure 1:
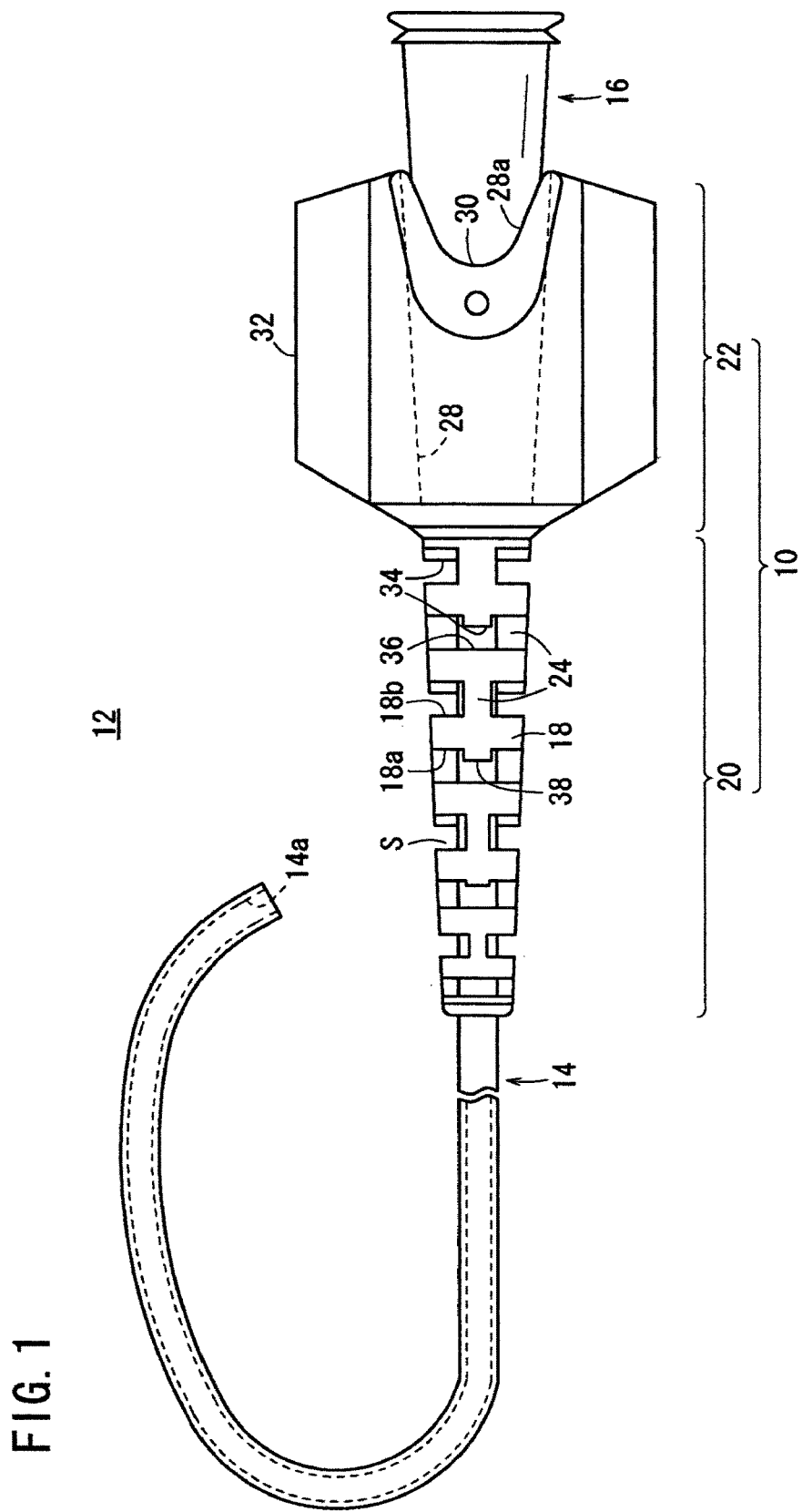
FIG. 1 is a schematic lateral view showing the general configuration of a catheter provided with a strain relief according to an embodiment made in accordance with principles of the disclosed subject matter.

FIG. 1 is a schematic lateral view showing the general configuration of a guiding catheter 12 provided with a strain relief 10 according to this embodiment. As shown in FIG. 1, the strain relief 10 is provided on a guiding catheter 12 (hereinafter referred also to simply as catheter 12) having a long shaft section 14 (tubular body) formed to be hollow. The guiding catheter 12 is used, for example, for PTCA (Percutaneous Transluminal Coronary Angioplasty) in which a stenosed part of a blood vessel is treated by dilating it.

In this case, the catheter 12 is inserted into a meandering blood vessel (e.g., aorta) through an insertion instrument or the like (not shown), and a distal portion of the catheter 12 is delivered to a predetermined site (e.g., entrance of a coronary artery or the like). Thereafter, a balloon catheter (not shown) or the like is inserted into the inside (lumen 14a) of the shaft section 14, and the balloon catheter is guided from the entrance of the coronary artery or the like into a stenosed part generated in the coronary artery or the like. The balloon of the balloon catheter is inflated in the stenosed part, whereby the blood vessel (stenosed part) can be treated. Incidentally, the catheter 12 according to the presently disclosed subject matter is not restricted to use for such PTCA; naturally, the catheter 12 may be used for improvement or diagnosis of a lesion formed in a living body organ, for example, other blood vessels such as peripheral vessels in limbs or vessels in the cranial or cervical part, bile duct, trachea, esophagus, urethra, etc.

More specifically, the catheter 12 according to this embodiment can include: the shaft section 14 having a small diameter and extending in an axial direction (e. along a longitudinal axis of the shaft section 14); a hub 16 connected (linked) to a proximal portion of the shaft section 14; and strain relief 10 provided at a connection part between the shaft section 14 and the hub 16. The overall length of the catheter 12 (the distance from the distal end of the shaft section 14 to the proximal end of the hub 16) is set, for example, in the range of about 65 to 135 cm, taking into account the operability (maneuverability) of the catheter 12.

The shaft section 14 is formed in a hollow cylindrical shape from a highly slidable resin or the like, and has the hollow lumen 14a extending in the axial direction. A guide wire (not shown) for guiding the catheter 12 to the entrance of a coronary artery or the like or a balloon catheter for therapy of a stenosed part or the like is inserted in the lumen 14a. In addition, the shaft section 14 has adequate flexibility and adequate strength so that the operator (user of the catheter 12) can smoothly deliver the shaft section 14 into a living body organ such as a blood vessel, while gripping and operating the proximal side of the shaft section 14. In this case, examples of the material for forming the shaft section 14 include polymeric materials such as polyolefins (e.g., polyethylene, polypropylene, polybutene, ethylene-propylene copolymers, ethylene-vinyl acetate copolymers, ionomers, or mixtures of two or more of them), polyvinyl chloride, polyamides, polyamide elastomers, polyurethane, polyurethane elastomers, polyimides, fluoro-resins, etc. and mixtures of them. Alternatively, the shaft section 14 may be formed as a multi-layer tube or the like using two or more of these polymeric materials.

The length of the shaft section 14 is determined based on the length of the blood vessel from the position of insertion of the shaft section 14 into a living body to the entrance of the coronary artery or the like. For example, where the overall length of the catheter 12 is 100 cm, the length of the shaft section 14 may favorably be set to about 96 cm.

The hub 16 connected to the proximal side of the shaft section 14 can be transparent, and made from a resin or the like. This ensures that the guide wire or the like inserted in the lumen of the catheter 12 can be visually checked or confirmed. The rigidity (hardness) of the hub 16 can be higher than that of the shaft section 14. Examples of the material constituting the hub 16 include thermoplastic resins such as polycarbonates, polyamides, polysulfones, polyarylate, and methacrylate-butylene-styrene copolymers.

The hub 16 is formed in a hollow cylindrical shape, and is engaged with and held by a proximal portion of the strain relief 10. The hollow cylindrical inside (not shown) of the hub 16 communicates with the lumen 14a, attendant on the connection between the hub 16 and the shaft section 14. The above-mentioned guide wire or balloon catheter or the like can be inserted into a proximal-side opening of the hollow cylindrical inside of the hub 16. The hub 16 can be formed in a tapered shape such that the diameter is gradually increased along the direction from the distal end toward the proximal end. This enables the guide wire or balloon catheter or the like to be easily inserted via the proximal-side opening and be easily guided into the lumen 14a of the shaft section 14. Incidentally, the shape of the hub 16 is not restricted to the hollow cylindrical shape but may be a tubular shape which has an angular (inclusive of polygonal) cross-sectional shape.

Figure 2:
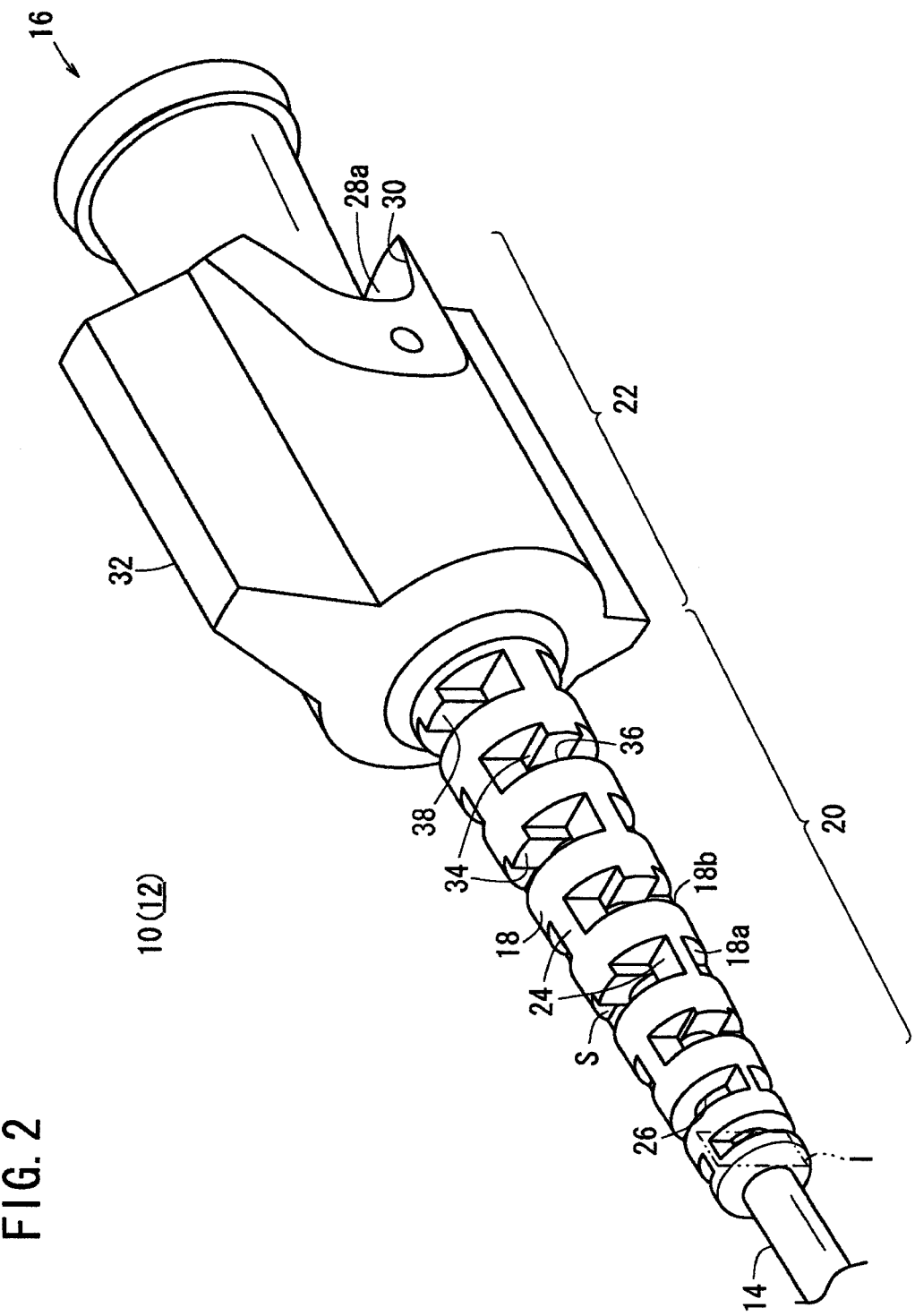
FIG. 2 is a perspective view showing, in enlarged form, the vicinity of the strain relief of FIG. 1.

FIG. 2 is a perspective view showing, in enlarged form, the vicinity of the exemplary strain relief 10 of FIG. 1. As shown in FIG. 2, the strain relief 10 is provided at the connection part between the shaft section 14 and the hub 16 of the catheter 12 (at a proximal portion of the shaft section 14). The strain relief 10 is composed of a curving section 20 in which a plurality of enclosing parts 18 for enclosing (surrounding) the outer circumferential surface of the shaft section 14 are arranged in the axial direction, and a tubular holding section 22 (proximal-side end portion) which is continuous with and on the proximal side of the curving section 20. The material constituting the strain relief 10 can be selected from those materials which are intermediate between the shaft section 14 and the hub 16 in rigidity and are rich in elasticity. Specific examples of the material include polyolefin elastomers, polyamide elastomers, and polyester elastomers.

The curving section 20 of the strain relief 10 has interconnecting parts 24 for coupling the enclosing parts 18 to each other, the interconnecting parts 24 located between the plurality of the enclosing parts 18 and arranged along the axial direction. Therefore, the curving section 20 is integrally formed so that the enclosing parts 18 and the interconnecting parts 24 are alternately arranged in succession. Furthermore, a space portion S is formed (defined) between each adjacent pair of the enclosing parts 18 of the curving section 20 (on lateral sides of the interconnecting part 24 extending in the axial direction).

The enclosing part 18 is formed in an annular shape, and the inside diameter of a hole 26 provided in a central portion thereof is approximately equal to the outside diameter of the shaft section 14. A proximal portion of the shaft section 14 is fitted into the enclosing parts 18 so as to penetrate the holes 26, whereby it is disposed at the axis of the curving section 20 (the plurality of enclosing parts 18 aligned in the axial direction). In addition, the plurality of enclosing parts 18 aligned along the axial direction are so formed that the outside diameter thereof gradually increases from the distal side toward the proximal side and, therefore, the curving section 20 has a tapered shape. In this case, the holes 26 of the enclosing parts 18 are constant in inside diameter, while the annular portions of the enclosing parts 18 are gradually enlarged in radial length thereof.

Besides, each of the interconnecting parts 24 extends in the axial direction between the adjacent enclosing parts 18, and is continuous with the opposed end faces (a distal end face 18a and a proximal end face 18b) of the enclosing parts 18. One pair of the interconnecting parts 24 are disposed in one space portion S (the area between the two enclosing parts 18) at positions which are opposite to each other with the shaft section 14 therebetween. The interconnecting parts 24 are so formed as to freely deform elastically relative to the axis of the curving section 20. One pair of interconnecting parts 24 enable the enclosing parts 18 to swing in a direction roughly orthogonal to an imaginary plane I (see FIG. 2) defined by the one pair of interconnecting parts 24.

The interconnecting parts 24 arranged in plurality in the axial direction are so disposed that the interconnecting parts 24 located adjacent to each other with the enclosing part 18 therebetween are deviated from each other by 90 degrees along the circumferential direction. As a result, the interconnecting parts 24 can surround (enclose) the proximal portion of the shaft section 14 at angular intervals of 90 degrees, thereby giving desired flexibility to the shaft section 14 so that the shaft section 14 can be freely curved.

In addition, the plurality of interconnecting parts 24 aligned in the axial direction are so formed that the cross-sectional area thereof increases. In other words, a columnar part interconnecting the enclosing parts 18 is gradually enlarged, from the distal side toward the proximal side. Accordingly, the interconnecting parts 24 are higher in strength (elasticity) on the proximal side (near the holding section 22) than on the distal side.

On the other hand, the holding section 22 continuous to and located on the proximal side of the curving section 20 extends in the axial direction so as to be shorter than the curving section 20, and is formed therein with an accommodation space 28 (accommodation part) in which to accommodate a distal portion of the hub 16. The accommodation space 28 opens on the proximal side of the holding section 22, and the hub 16 is inserted into the accommodation section 22 via a proximal-side opening 28a. The holding section 22 can be formed with a cutout 30 on the proximal side thereof. The cutout 30 functions to facilitate inflation of the proximal-side opening 28a, and to aid insertion of the hub 16. The holding section 22 can hold the hub 16 (fitted therein) by inserting a distal portion of the hub 16 deep into the accommodation space 28, whereby it is made possible to handle the hub 16 and the strain relief 10 as one body.

The holding section 22 can include a pair of wings 32 (wing-shaped parts) formed at anouter circumferential surface and extending in the axial direction. When the operator manipulates the catheter 12, the pair of wings 32 enable the operator to easily grip the catheter 12, whereby operability can be enhanced.

Figure 3A:
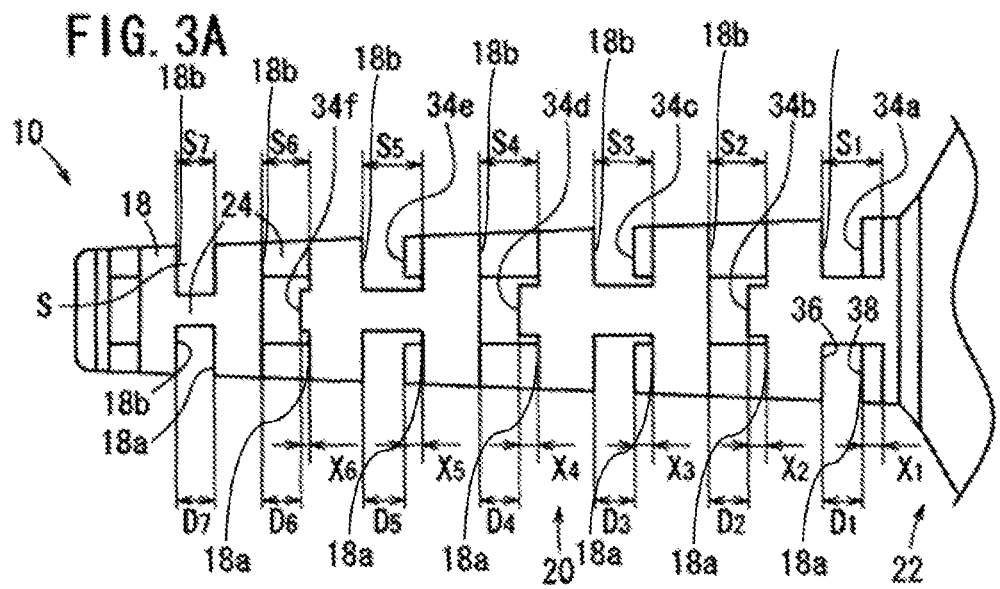
FIG. 3A is an enlarged lateral view showing a curving section of the strain relief of FIG. 1.
Figure 3B:
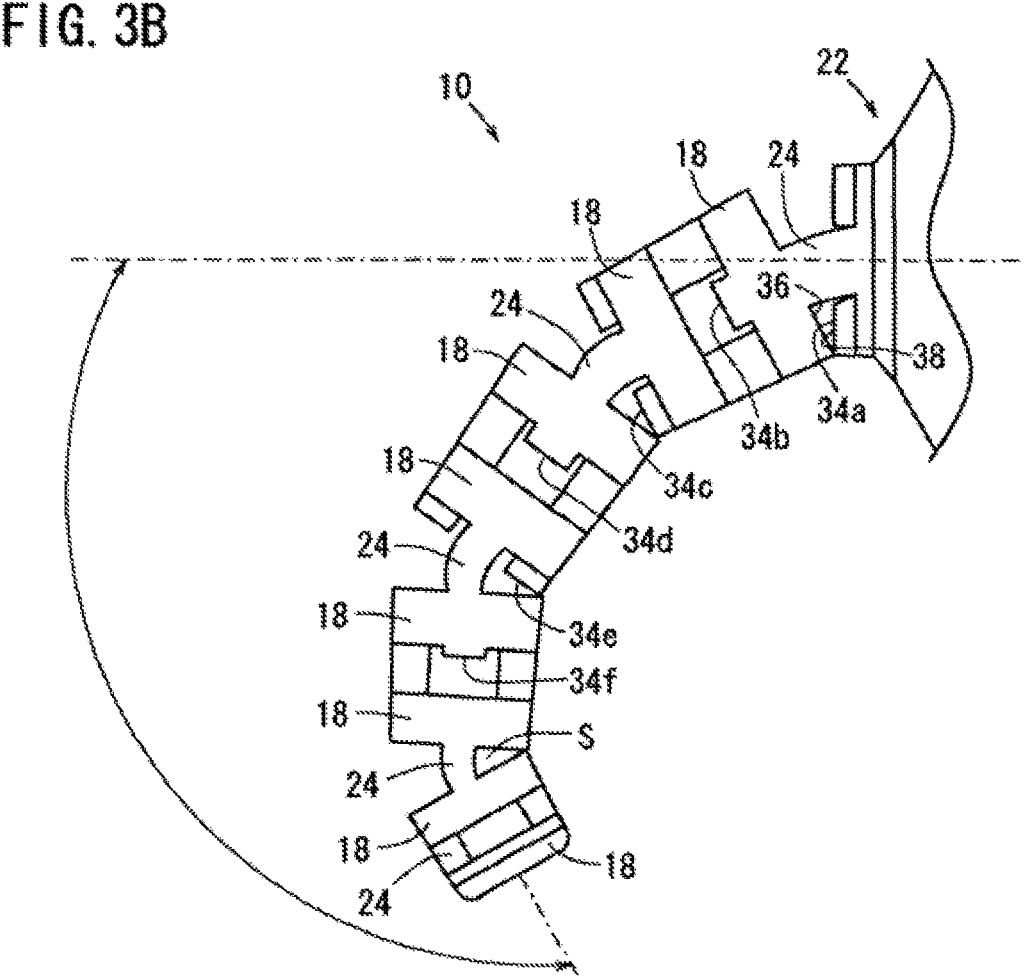
FIG. 3B is an enlarged lateral view showing a curved state of the strain relief changed from the state of FIG. 3A.

FIG. 3A is an enlarged lateral view showing the curving section 20 of the strain relief 10 shown in FIG. 1, and FIG. 3B is an enlarged lateral view showing a curved state of the strain relief 10 changed from the state shown in FIG. 3A. Incidentally, in FIGS. 3A and 3B, the catheter 12 (shaft section 14) is omitted from the drawing, for easy understanding of the operation of the strain relief 10.

As shown in FIG. 3A, the space portion S formed between each adjacent pair of enclosing parts 18 is formed (defined) on a lateral side of the pair of interconnecting parts 24 extending in the axial direction. Therefore, the width of the space portions S in the axial direction is set by the axial length of the interconnecting parts 24.

The space portions S are defined in plurality along the axial direction of the curving section 20, by the plurality of enclosing parts 18 aligned in the axial direction (in FIG. 3A, the plurality of space portions S are denoted by reference signs S1 to S7, in this order from the proximal side toward the distal side). In this case, the axial lengths of the plurality of space portions S1 to S7 are so set that the space portion S1 on the proximal side is greater than the space portion S7 on the distal side in axial length (in a length parallel with a longitudinal axis of the strain relief 10), and the space portions S2 to S6 therebetween are gradually reduced in axial length from the proximal side toward the distal side. In other words, the curving section 20 is so formed that the interconnecting parts 24 are increased in cross-sectional area along the proximal direction and, attendantly, the interconnecting parts 24 on the proximal side are greater in axial length than the interconnecting parts 24 on the distal side. This ensures that the plurality of interconnecting parts 24 aligned in the axial direction are elastically deformed evenly and easily, and the curving section 20 as a whole can be well-balanced in regard of flexibility.

In addition, the enclosing parts 18 of the strain relief 10 according to this embodiment are formed with projections 34 that project into the space portions S1 to S7 (in FIG. 3A, the plurality of projections 34 are denoted by reference signs 34a to 34f, in this order from the proximal side toward the distal side). The projections 34a to 34f are formed to rise (project) in the distal direction from the distal end faces 18a of the enclosing parts 18, correspondingly. One pair of the projections 34 are formed in each space portion S. The one pair of projections 34 are so provided as to be located at circumferential-directionally middle positions between the one pair of interconnecting parts 24.

When the strain relief 10 (curving section 20) is curved (e.g., during use), the projection 34 comes into contact with the proximal end face 18b of the enclosing part 18 which moves in the space portion S to be proximate thereto (hereinafter that part of the proximal end face 18b which is contacted by the projection 34 will be referred to as contact face 36). Therefore, the projections 34 determine the moving amounts (amounts of curvature) of the enclosing parts 18, whereby the degree of curvature of the axially aligned enclosing parts 18 as a whole (namely, the curving section 20) can be regulated.

The projections 34 can each be continuous with the outer circumferential surface of the enclosing part 18. This ensures that each projection 34 comes into contact with a portion, near the outer circumference, of the contact face 36 opposed thereto. In view of this, the projections 34 can be formed in a suppressed projection amount.

Furthermore, the projections 34a to 34f can be configured such that the projection amount X1 of the enclosing part 18 on the proximal side is large, and the projection amounts X2 to X6 of the projections 34b to 34f in this order from the proximal side toward the distal side are in the gradually decreasing order. In addition, in the space portion S7 on the distal side, a projection 34 itself can be absent, and the distal end face 18a of the enclosing part 18 is formed flat. In other words, the projections 34a to 34f have their projection amounts X1 to X6 set according to the axial lengths of the space portions S1 to S7. The distances D1 to D6 from the end faces 38 of the projections 34a to 34f to the contact faces 36 are equal to the axial length (distance D7) of the space portion S7. Thus, the distance D7 of the space portion S7 is equal to the distances D1 to D6 from the end faces 38 of the projections 34 to the contact faces 36. This ensures that the variation amounts of the plurality of space portions S1 to S7 aligned in the axial direction (the amounts of curvature between the enclosing parts 18) are made even.

In addition, the end faces 38 of the projections 34 and the contact faces 36 (proximal end faces 18b) of the enclosing parts 18 can both be formed flat. The proximal end faces 18b have a substantially planar surface with no recess formed therein. This ensures that when the strain relief 10 is curved, the flat end faces 38 and the flat contact faces 36 make contact with each other, so that the strain relief 10 can be curved favorably, with torsion or the like restrained.

The strain relief 10 and the catheter 12 provided with the strain relief 10, according to this embodiment, are fundamentally configured as described above. Now, operation and effect of the strain relief 10 will be described below.

One surgery that can be conducted using the catheter 12 according to this embodiment, for example, is the Seldinger catheter technique. In this case, a guide wire is initially introduced into a blood vessel from a femoral region or the like, and the shaft section 14 of the catheter 12 is inserted into the blood vessel along the guide wire.

Then, the operator (user of the catheter 12), while gripping the shaft section 14 of the catheter 12 and the holding section 22 of the strain relief 10, advances the shaft section 14 along the guide wire into the blood vessel. In this case, the shaft section 14 introduced into the blood vessel is advanced while bending according to the meandering blood vessel shape. After the catheter 12 has arrived at a target site, a therapeutic device such as a balloon catheter can be inserted into the lumen of the catheter 12 via the proximal end of the catheter 12. In some situations, a device such as Y-connector (not shown) may be connected to the proximal end of the hub 16 of the catheter 12. In such a case, the therapeutic device such as a balloon catheter is inserted via the proximal end of the Y-connector. In these cases, the user of the catheter 12 operates the catheter 12 inserted in the patient's body from above the catheter 12, so that an upward force is exerted on the proximal end of the catheter 12 or on the proximal end of the catheter 12 connected with the Y-connector. When a stress is thus exerted on the connection part between the shaft section 14 and the hub 16 and the connection part is bent by the stress, the stress is transmitted to cause an elastic deformation of the curving section 20 of the strain relief 10. The strain relief 10 can cause an anti-kinking property to be exhibited at the connection part between the shaft section 14 and the hub 16, and can disperse the stress concentrated on the connection part.

To be more specific, when a stress is transmitted from the connection part between the shaft section 14 and the hub 16 to the strain relief 10, the interconnecting parts 24 are elastically deformed, causing the interconnected enclosing parts 18 to be moved in a direction (e.g., downward direction in FIG. 3B) different from the axial direction. In other words, in the strain relief 10, the projection 34 formed at the distal end face 18a of the enclosing part 18 and the contact face 36 of the enclosing part 18 opposed to the projection 34 come closer to each other, whereby the space portion S is reduced in axial length. In this instance, the interconnecting part 24 on the proximal side having a larger cross-sectional area and being longer in the axial direction and the interconnecting part 24 on the distal side having a smaller cross-sectional area and being shorter in the axial direction have substantially the same degrees of elasticity, so that the plurality of enclosing parts 18 aligned in the axial direction are curved evenly. Consequently, exertion of a high stress on one or some of the interconnecting parts 24 can be obviated.

As shown in FIG. 3B, when a further stress is exerted on the strain relief 10, the interconnecting part 24 can be elastically deformed to a great extent, resulting in the end face 38 of the projection 34 and the contact face 36 of the enclosing part 18 making contact with each other. In other words, the projection 34 inhibits the enclosing part 18 from further curving. Thus, the degree of curvature of the curving section 20 having the plurality of enclosing parts 18 aligned in the axial direction is determined by the projections 34. In this instance, one pair of projections 34 can be formed at circumferential-directionally middle positions between one pair of interconnecting parts 24, so that the contact between the enclosing part 18 and the projection 34 takes place at a position spaced most from the pair of interconnecting parts 24. Consequently, that portion of the enclosing part 18 which exhibits a large moving amount can be favorably supported (contacted) by the projection 34.

In addition, the amount of curvature of the enclosing part 18 (or the degree of curvature of the curving section 20) can be regulated according to the projection amount X of the projection 34. Therefore, it is possible not only to curve the curving section 20 by 90 degrees or more relative to the axis of the strain relief 10, as shown in FIG. 3B, but also to suppress the degree of curvature equal or less than 90 degrees.

As described above, the distances D1 to D6 from the end faces 38 of the projections 34 to the contact faces 36 of the enclosing parts 18 can be set substantially equal. Therefore, in the condition where the projections 34 and the enclosing parts 18 are in contact with each other, the variation amounts of the plurality of space portions S1 to S7 (the amounts of curvature of the enclosing parts 18) can be evened. Accordingly, the stress exerted on the strain relief 10 can be substantially or entirely dispersed, whereby durability of the strain relief 10 can be enhanced.

FIG. 4A is a lateral view showing a strain relief 10A according to a first modification of the presently disclosed subject matter, and FIG. 4B is a lateral view showing a strain relief 10B according to a second modification of the presently disclosed subject matter.

As shown in FIG. 4A, the strain relief 10A according to the first modification differs from the strain relief 10 according to the first embodiment in that the projections 34 are provided on the side of the proximal end face 18b of the enclosing part 18. Specifically, the projection 34 provided on the side of the proximal end face 18b of the enclosing part 18 and the distal end face 18a of the enclosing part 18 opposed to the projection 34 come into contact with each other. In this case, also, the curving of the enclosing parts 18 is inhibited at predetermined distances D1 to D7 by the projections 34. Therefore, the degree of curvature of the curving section 20 as a whole can be regulated, like in the case of the strain relief 10 of FIG. 1.

In addition, as another modification, the projections 34 may naturally be provided at both end faces (the distal end face 18a and the proximal end face 18b) of each enclosing part 18. In this case, the projections 34 on the side of the distal end face 18a and the projections 34 on the side of the proximal end face 18b, of the adjacent enclosing parts 18, may be so disposed as to face each other or may be disposed at positions deviated from each other in the circumferential direction.

As a further modification, in the case where the projections 34 are provided at both end faces (the distal end face 18a and the proximal end face 18b) of each enclosing part 18, a plurality of projections 34 may be disposed at the end face on one side, or pluralities of projections 34 may be disposed at both end faces. In this case, the plurality of projections 34 at the end face on one side may be so disposed such that the projection 34 at the end face on the other side is located therebetween.

As shown in FIG. 4B, the strain relief 10B according to the second modification differs from the strain reliefs 10 and 10A according to the first embodiment and the first modification in that an enclosing part 18 is spirally wound around the connection part between the shaft section 14 and the hub 16, and projections 34 are provided at circumferential-directionally predetermined positions (at angular intervals of 90 degrees) on the side of the distal end face 18a. Thus, the strain relief 10B has no interconnecting part 24. With the enclosing part 18 thus formed spirally, also, it is possible to cause an anti-kinking property to be exhibited, and to regulate the degree of curvature of the curving section 20 by the projections 34. Incidentally, while the end faces 38 of the projections 34 are inclined according to the spiral shape of the enclosing part 18 in FIG. 4B, this naturally is not restrictive.

As described above, the catheter 12 according to the presently disclosed subject matter has such a configuration that when the strain relief 10 is curved, the projections 34 that project from the enclosing parts 18 come into contact with the enclosing parts 18 opposed to the projections 34, so that the variation amounts of the space portions S can be easily changed. Specifically, the projections 34 determine the amount of curvature between the adjacent enclosing parts 18, whereby the degree of curvature of the strain relief 10 can be regulated, while maintaining the flexibility of the strain relief 10. In the strain relief 10, therefore, the connection part between the shaft section 14 and the hub 16, which differ in hardness, can be prevented from excessively bending, while permitting the connection part to exhibit a sufficient anti-kinking property. As a result, the strain relief 10 ensures that when the operator inserts a therapeutic device into the catheter 12 or into a device such as a Y-connector connected to the proximal end of the catheter 12, the operating force exerted in the direction toward the user can be reduced. In addition, the force applied for advancing or withdrawing or rotating the catheter 12 can be easily transmitted from the holding section 22 to the shaft section 14. Consequently, operability of the catheter 12 can be enhanced.

When the projections 34 are each formed at a position that is continuous with the outer circumferential surface of the enclosing part 18, it is possible to set the projection amounts of the projections 34 to be as small as possible, while realizing a desired degree of curvature when the strain relief 10 is curved. As a result, rigidity of the projections 34 can be easily secured, and the strain relief 10 can be easily formed.

Further, with the pairs of interconnecting parts 24 so formed that they are gradually increased in cross-sectional area from the distal side toward the proximal side, the strength of the strain relief 10 on the proximal side can be enhanced to a greater degree. In addition, where the pairs of interconnecting parts 24 which are adjacent to each other with the enclosing part 18 therebetween are so located as to be deviated from each other by about 90 degrees along the circumferential direction, the interconnecting parts 24 can surround (enclose) the shaft section 14 at angular intervals of 90 degrees. This enables the shaft section 14 to be curved substantially evenly in all directions.

Furthermore, with the shaft section 14 and the hub 16 of the catheter 12 provided as separate bodies, they can be formed from different materials. Therefore, the shaft section 14 and the hub 16 can be easily designed to have respective desired values of hardness, and the shaft section 14 and the hub 16 thus differing in hardness can be easily connected by the strain relief 10. In addition, it is not necessary to provide any wing on the side of the hub 16 which is engaged with and held by the holding section 22. This makes it possible to shorten the proximal portion (hub 16) of the catheter 12, and to suppress a rise in cost.

The presently disclosed subject matter is not restricted to the above-described embodiments and modifications, and, naturally, various configurations can be adopted within the scope of the gist of the presently disclosed subject matter. For instance, in the strain reliefs 10, 10A and 10B in the above-described embodiments and first and second modifications, the pairs of projections 34 are provided at angular intervals of 90 degrees so that the projections 34 at every other stages (pairs) in the axial direction are arranged in register. This arrangement, however, is not restrictive. For example, the projections 34 may be formed to be shifted by a predetermined angle (e.g., 30 degrees) along the circumferential direction per turn (circumference) of the enclosing part(s) 18.

The strain relief 10, 10A, 10B according to the presently disclosed subject matter can be applied not only to the above-mentioned guiding catheters 12 but also to balloon catheters, angiography catheters, or master catheters and sub catheters or the like to be inserted via a Y-connector or the like. The strain relief 10, 10A, 10B can be provided not only on the catheter 12 but also at a joint part between two members differing in hardness.

It will be apparent to those skilled in the art that various modifications and variations can be made in the presently disclosed subject matter without departing from the spirit or scope of the presently disclosed subject matter. Thus, it is intended that the presently disclosed subject matter cover the modifications and variations of the presently disclosed subject matter provided they come within the scope of the appended claims and their equivalents. All related art references described above are hereby incorporated in their entirety by reference.

What is claimed is:

1. A strain relief having a curving section and a holding section, the curving section having a plurality of enclosing parts arranged in an axial direction and enclosing a longitudinal axis of the strain relief, the strain relief including a plurality of space portions located between adjacent enclosing parts that allow the strain relief to be freely bendable and curved about any radial angle with respect to the longitudinal axis of the strain relief, including an interconnecting part, wherein the adjacent enclosing parts are each interconnected by the interconnecting part extending in the axial direction, wherein a first adjacent enclosing part includes a first flat shaped surface facing a distal end of the strain relief and is disposed directly opposite to an opposing flat shaped surface facing a proximal end of the strain relief of an adjacent enclosing part, wherein the first flat shaped surface includes a non-interlocking projection (i) having a flat shaped end face facing the distal end of the strain relief and (ii) projecting from the flat shaped-first flat shaped surface toward the opposing flat shaped surface of the adjacent enclosing part, wherein the opposing flat shaped surface is a substantially planar surface with no recess located therein such that during bending the flat shaped end face of the non-interlocking projection abuts the planar surface of the opposing flat shaped surface thereby inhibiting the enclosing parts from further curving along the longitudinal axis, wherein there is a gap between the flat shaped end face of the non-interlocking projection and the opposing flat shaped surface in a non-strained state, wherein the non-interlocking projection projects in a direction substantially parallel to the longitudinal axis, and wherein the flat shaped end face of the non-interlocking projection has the flat shape across an entire width of the non-interlocking projection.

2. The strain relief according to claim 1, wherein the non-interlocking projection is continuous with an outer circumferential portion of at least one of the adjacent enclosing parts.

3. The strain relief according to claim 1, further comprising a non-interlocking projection located on a second flat shaped surface disposed directly opposite to the opposing flat shaped surface of the adjacent enclosing part.

4. The strain relief according to claim 1, wherein the plurality of space portions are formed in the axial direction and each have an axial equal length substantially parallel to the longitudinal axis of the strain relief, the axial length being defined as a length between an end surface of the non-interlocking projection and the directly opposed surface.

5. The strain relief according to claim 4, wherein a set distance for a first space portion in the plurality of spaced portions of the strain relief is substantially equal in length with respect to a second space portion in the plurality of spaced portions.

6. The strain relief according to claim 1, wherein the adjacent enclosing parts are each interconnected by one of a plurality of pairs of interconnecting parts extending in the axial direction,
the pairs of the interconnecting parts are arranged alternately with the enclosing parts in the axial direction, and gradually increase in cross-sectional area along the axial direction from a distal side toward a proximal side.

7. The strain relief according to claim 6, wherein the pairs of the interconnecting parts which are adjacent to each other with the enclosing parts therebetween are deviated from each other by substantially 90 degrees along a circumferential direction.

8. The strain relief according to claim 1, wherein there are a plurality of non-interlocking projections and each has a length in a direction substantially parallel with the longitudinal axis, and lengths of the lion-interlocking projections are different from each other.

9. The strain relief according to claim 8, wherein the length of each of the non-interlocking projections decreases from a proximal portion projection to a distal portion projection of the strain relief.

10. A catheter comprising a strain relief, the strain relief including a plurality of enclosing parts arranged in an axial direction and enclosing a longitudinal axis of the strain relief, the strain relief including a plurality of space portions formed between adjacent enclosing parts that allow the strain relief to be freely bendable and curved about any radial angle with respect to the longitudinal axis of the strain relief, including a pair of interconnecting parts disposed between each of the adjacent enclosing parts, wherein a first adjacent enclosing part includes a first flat shaped surface facing a distal end of the strain relief and is disposed directly opposite to an opposing flat shaped surface facing a proximal end of the strain relief of an adjacent enclosing part, wherein the first flat shaped surface includes a non-interlocking projection (i) having a flat shaped end face facing the distal end of the strain relief and (ii) projecting from the first flat shaped surface toward the opposing flat shaped surface of the adjacent enclosing part, wherein there is a gap between the flat shaped end face of the non-interlocking projection and the opposing flat shaped surface in a non-strained state, wherein the non-interlocking projection projects in a direction substantially parallel to the longitudinal axis, wherein the opposing flat shaped surface is a substantially planar surface extending from a first of the interconnecting parts to a second of the interconnecting parts such that the opposing flat shaped surface has no recess located therein and during bending the flat shaped end face of the non-interlocking projection abuts the planar surface of the opposing flat shaped surface to inhibit the enclosing parts from further curving, wherein the catheter includes a tubular body extending in the axial direction and having a hollow interior, and a hub connected to a proximal portion of the tubular body, wherein the flat shaped end face of the non-interlocking projection has the flat shape across an entire width of the non-interlocking projection, and wherein the enclosing parts of the strain relief encloses an outer circumference of a proximal portion of the tubular body so as to dispose the tubular body at the longitudinal axis, and has a proximal-side end portion of the strain relief engaged with the hub so that a distal side end portion of the strain relief can be freely bent relative to the hub.

11. The catheter according to claim 10, wherein the tubular body and the hub are composed as separate bodies, and
the proximal-side end portion of the strain relief includes a wing-shaped part operable to rotate the catheter, and an accommodation part in which the hub is detachably engaged and held.

12. The catheter according to claim 10, wherein the non-interlocking projection projects at a position continuous with an outer circumferential surface of at least one of the adjacent enclosing parts.

13. The catheter according to claim 10, wherein the non-interlocking projection of each of the enclosing parts has a length in a direction substantially parallel with the longitudinal axis, and the length of a first non-interlocking projection is different from the length of a second adjacent non-interlocking projection.

14. The catheter according to claim 10, further comprising a non-interlocking projection located on a second flat shaped surface disposed on the first adjacent enclosing part and directly opposite to the opposing flat shaped surface of the adjacent enclosing part.

15. The catheter according to claim 10, wherein the plurality of the space portions are formed in the axial direction and each have an axial length in the axial direction substantially parallel with the longitudinal axis, the axial length defined between the flat shaped end face of the non-interlocking projection that is directly opposed and spaced at a set distance from one of the first flat shaped surface and the opposing flat shaped surface.

16. The catheter according to claim 15, wherein the set distance for a first space portion of the plurality of space portions of the strain relief is substantially equal in length to a second space portion of the plurality of space portions.

17. The catheter according to claim 10, wherein the adjacent enclosing parts are each interconnected by one of a plurality of pairs of interconnecting parts extending in the axial direction, and
the pairs of the interconnecting parts are arranged alternately with the enclosing parts in the axial direction, and gradually increase in cross-sectional area along the axial direction from a distal side toward a proximal side.

18. The catheter according to claim 17, wherein the pairs of the interconnecting parts which are adjacent to each other with the enclosing parts therebetween are deviated from each other by substantially 90 degrees along a circumferential direction.

* * * * *